United States Patent
Singleton et al.

(10) Patent No.: US 7,311,878 B2
(45) Date of Patent: Dec. 25, 2007

(54) METHOD AND APPARATUS FOR PRODUCING SYNERGISTIC BIOCIDE

(75) Inventors: Freddie L. Singleton, Switzerland, FL (US); Michael J. Mayer, Jacksonville, FL (US); Alexander W. Breen, Jacksonville, FL (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 11/509,141

(22) Filed: Aug. 24, 2006

(65) Prior Publication Data

US 2007/0049642 A1    Mar. 1, 2007

Related U.S. Application Data

(60) Provisional application No. 60/711,462, filed on Aug. 26, 2005.

(51) Int. Cl.
*C07F 1/76* (2006.01)

(52) U.S. Cl. .................. 422/37; 210/753; 210/754; 210/755; 210/756; 564/114; 564/118; 564/119

(58) Field of Classification Search ............... 564/114, 564/118, 119; 210/753, 754, 755, 756; 422/37
See application file for complete search history.

(56) References Cited

U.S. PATENT DOCUMENTS

| 1,850,057 | A | * | 3/1932 | Baker et al. ................ 423/413 |
|---|---|---|---|---|
| 2,678,258 | A | | 5/1954 | Haller ......................... 23/190 |
| 2,710,248 | A | | 6/1955 | Sisler et al. .................. 23/190 |
| 2,837,409 | A | | 6/1958 | Sisler et al. .................. 23/190 |
| 3,038,785 | A | | 6/1962 | Brande et al. ................ 23/190 |
| 3,488,164 | A | | 1/1970 | Grushkin et al. ............. 23/356 |
| 5,976,386 | A | | 11/1999 | Barak ......................... 210/756 |
| 6,132,628 | A | * | 10/2000 | Barak ......................... 210/756 |
| 6,478,973 | B1 | * | 11/2002 | Barak ......................... 210/756 |

* cited by examiner

*Primary Examiner*—Peter O'Sullivan
(74) *Attorney, Agent, or Firm*—Joanne Mary Fobare Rossi

(57) ABSTRACT

An apparatus and methods to produce synergistic mixtures (or combinations) of haloamines to control growth of microorganisms in aqueous systems are disclosed. The apparatus and methods to produce synergistic mixtures entails producing a batch quantity of a haloamine and converting part of the haloamine to a second haloamine species to form the synergistic mixture.

8 Claims, 5 Drawing Sheets

Figure 1. Diagram of apparatus used to produce batch quantities of synergistic mixtures of haloamines.
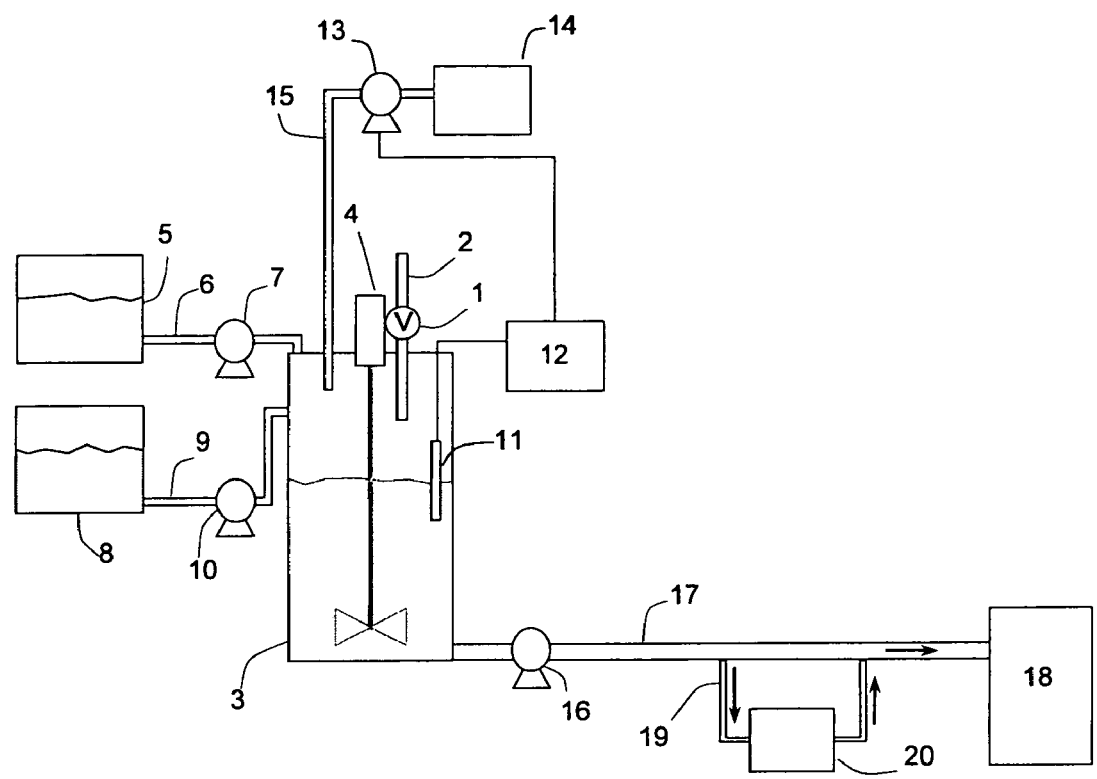

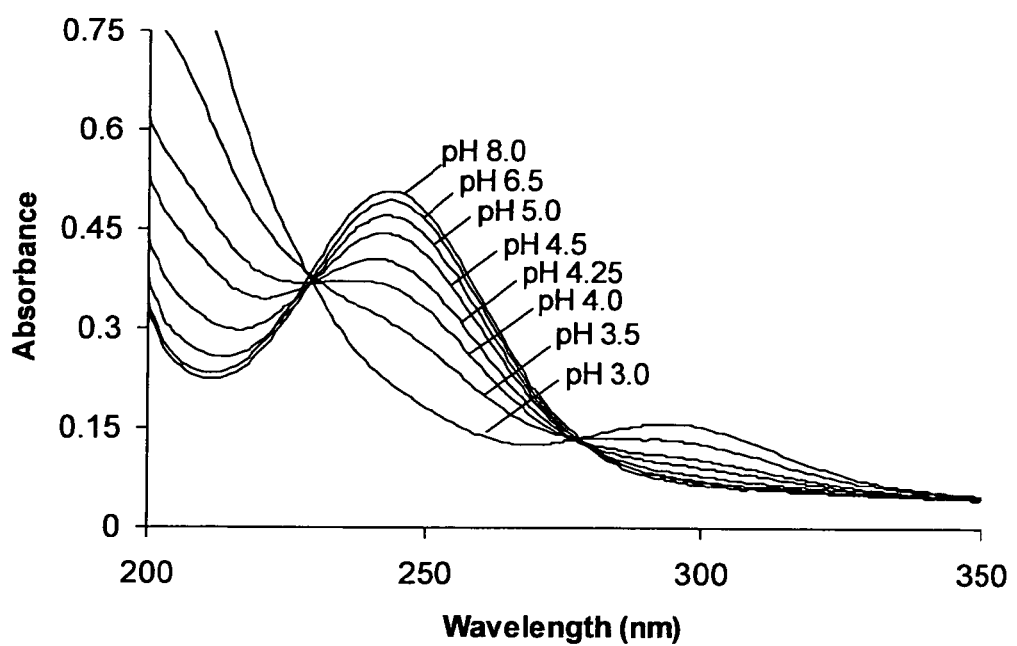
Figure 2. Absorbance spectra of a solution of 100 mg/l monochloramine I (as Cl-) at selected pH values.

Figure 3. Diagram of apparatus used to produce batch quantities of synergistic mixtures of haloamines.
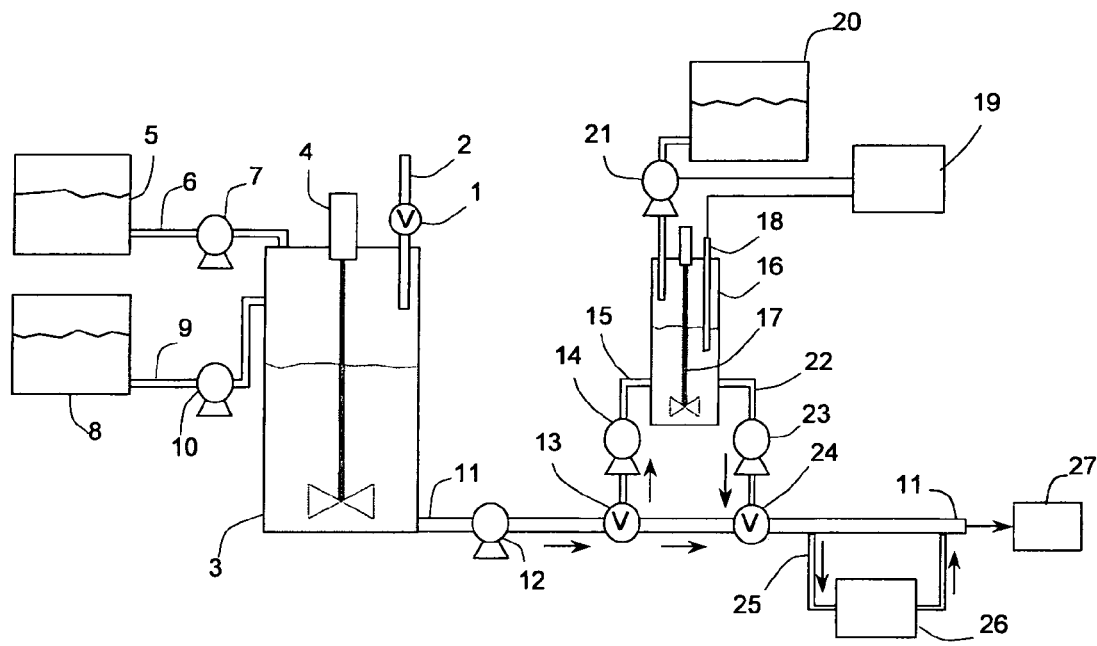

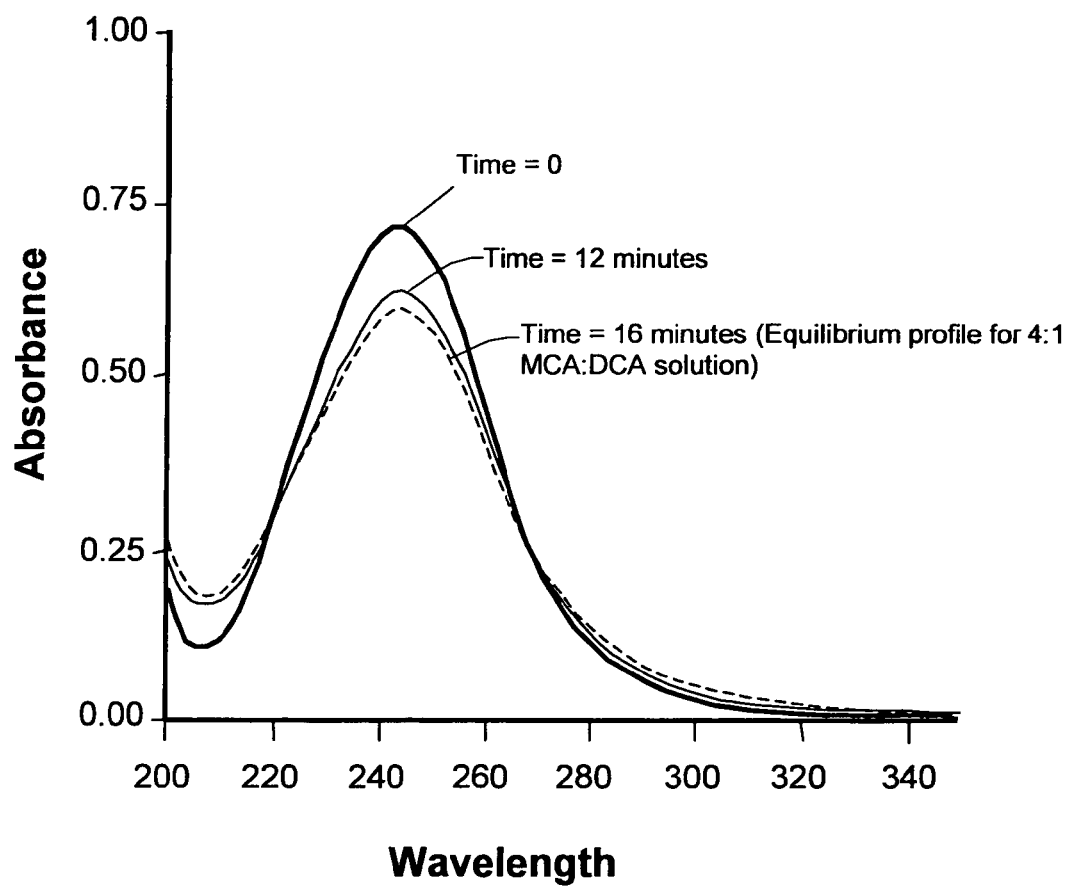
Figure 4. Change in absorbance spectrum of a batch solution of 1000 mg/l monochloramine I (as Cl-) as part of the solution stream is converted to dichloramine (200 mg/l as Cl-) by pH adjustment and reintroduced into the solution stream. The spectrum remained unchanged after the 16-minute scan. MCA = monochloramine, DCA = dichloramine.

Figure 5. Change in absorbance spectrum of a batch solution of 1000 mg/l monochloramine I (as Cl-) as part of the solution stream is converted to dichloramine (100 mg/l as Cl⁻) by pH adjustment and reintroduced into the solution stream. The spectrum remained unchanged after the 16-minute scan. MCA = monochloramine, DCA = dichloramine.
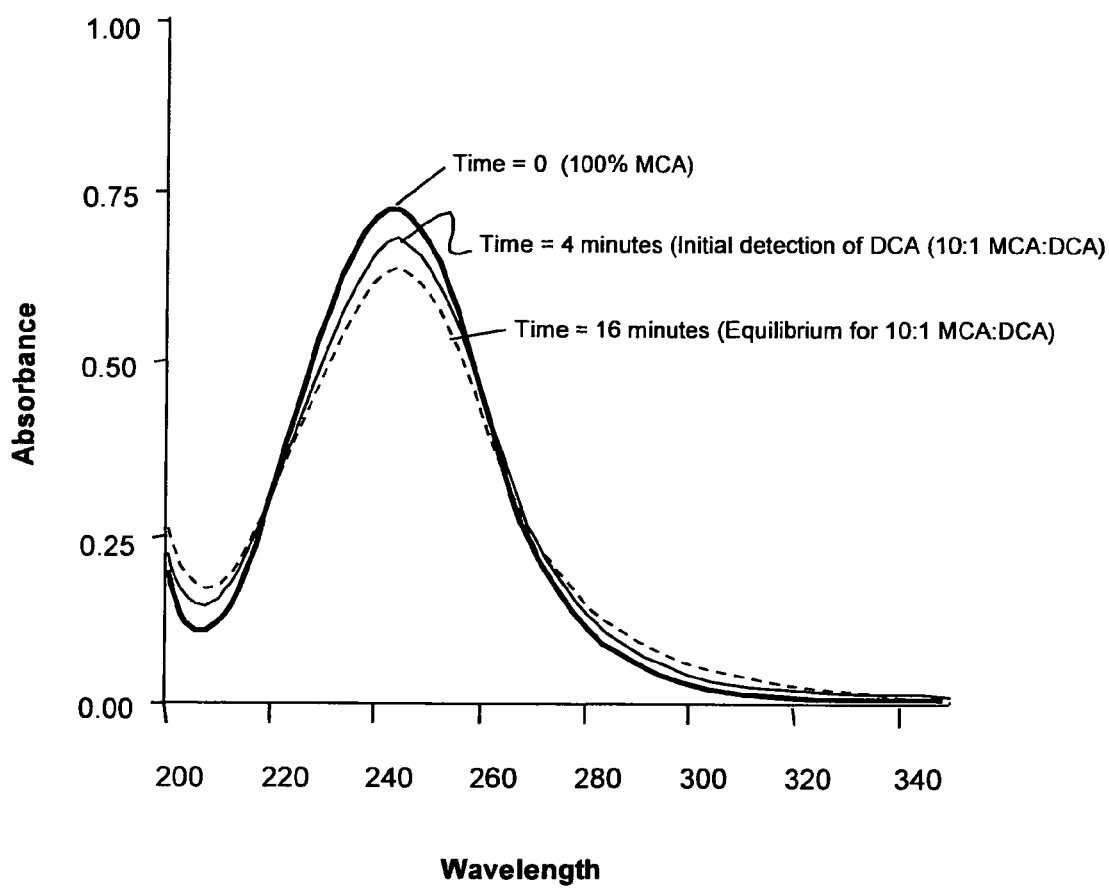

US 7,311,878 B2

METHOD AND APPARATUS FOR PRODUCING SYNERGISTIC BIOCIDE

This application claims the benefit of U.S. Provisional Application No. 60/711,462 filed Aug. 26, 2005, the entire contents is incorporated herein by reference.

TECHNICAL FIELD

The present invention relates to an apparatus and methods to produce mixtures (or combinations) of haloamines to control growth of microorganisms in aqueous systems, more particularly in industrial process waters, and most particularly in pulp and paper process systems.

BACKGROUND OF THE INVENTION

Uncontrolled growth of microorganisms in industrial production systems can have serious consequences such as lowered product quality, degradation or spoilage of products, contamination of products, and interference with a wide range of important industrial processes. Growth of microorganisms on surfaces exposed to water (e.g., recirculation systems, heat exchangers, once-through heating and cooling systems, pulp and paper process systems, etc.) can be especially problematic, as many of these systems provide an environment suitable for growth of bacteria and other types of microorganisms. Industrial process waters often provide conditions of temperature, nutrients, pH, etc. that allow for growth of microorganisms in the water and on submerged surfaces. Uncontrolled growth of microorganisms is often manifested in the water column with large numbers of free-floating (planktonic) cells as well as on submerged surfaces where conditions favor formation of biofilms.

Biofilm formation is a serious problem in aqueous industrial systems. The first stage of biofilm formation is planktonic cells contacting submerged surfaces either as a result of turbulence in water flow or by active movement toward the surface. If conditions are favorable for growth, microorganisms can attach to the surface, grow, and begin to produce exopolysaccharides that provide three-dimensional integrity to the biofilm. Over time, the biofilm becomes thicker and internally complex as cells reproduce and produce more exopolysaccharides. The microbial community of a biofilm can consist of single or multiple species.

Biofilms are seemingly ubiquitous in all natural, medical, and industrial settings where bacteria exist. Microorganisms can form biofilms on a wide variety of abiotic hydrophobic and hydrophilic surfaces, including glass, metals, and plastics.

Many types of processes, systems, and products can be adversely affected by uncontrolled growth of microorganisms in biofilms and in industrial process waters. Such problems include accelerated corrosion of metals, accelerated decomposition of wood and other biodegradable materials, restricted flow through pipes, plugging or fouling of valves and flow-meters, and reduced heat exchange or cooling efficiency on heat exchange surfaces. Biofilms may also be problematic relative to cleanliness and sanitation in medical equipment, breweries, wineries, dairies and other industrial food and beverage process water systems. Moreover, sulfate-reducing bacteria are often problematic in waters used for the secondary recovery of petroleum or for oil drilling in general. Although sulfate-reducing bacteria can form biofilms on equipment and in pipelines, the significant problem caused by these bacteria is that they generate metabolic by-products that have highly offensive odors, are toxic, and can cause corrosion of metal surfaces by accelerating galvanic action. For example, these microorganisms reduce sulfates present in the injection water to generate hydrogen sulfide, a highly toxic gas that has a highly offensive odor (i.e., rotten egg odor), is corrosive, and reacts with metal surfaces to form insoluble iron sulfide corrosion products.

Paper production is particularly susceptible to adverse effects of biofilms. Paper process waters have conditions (e.g., temperature and nutrients) that favor growth of microorganisms in the water and on exposed surfaces. Biofilms in paper process systems are often referred to as slime or slime deposits and contain paper fiber and other materials used in paper production. Slime deposits can become dislodged from system surfaces and become incorporated into the paper, which results in holes and defects or breaks and tears in the sheet. Such problems result in a lower quality product or unacceptable product being rejected. This necessitates stopping paper production to clean the equipment, which results in the loss of production time.

In order to control problems caused by microorganisms in industrial process waters, numerous antimicrobial agents (i.e., biocides) have been employed to eliminate, to inhibit or to reduce microbial growth. Biocides are used alone or in combination to prevent or control the problems caused by growth of microorganisms. Biocides are usually added directly to a process water stream typical method of addition is such that the biocide is distributed throughout the process system. In this manner, planktonic microorganisms and those in biofilms on surfaces in contact with the process water can be controlled.

Many organic and inorganic substances are used as biocides in industrial process systems. The type of biocide used in a given system will depend on many factors including, but not limited to, the nature of the medium to which the biocide is added, the problematic microorganism(s), as well as specific requirements of the industry, including safety and regulatory considerations.

Depending on their chemical composition and mode-of-action, biocides are classified as oxidizing or non-oxidizing. Oxidizing and non-oxidizing biocide can be used alone or in combination depending on the application. Oxidizing biocides have been widely used in industry for decades, especially in pulp and paper production where strong oxidizers have been used to control microbial populations. Oxidizing biocides such as chlorine gas, sodium hypochlorite, hypobromous acid, and chlorine dioxide are widely used as biocides to treat recirculating waters in many types of industries. Two of the primary reasons for using these and other oxidizing biocides is that such oxidizers are: (1) inexpensive; and (2) non-specific regarding which types of microorganisms are inhibited; if sufficient concentrations of oxidizing biocides are achieved virtually all microorganisms can be inhibited.

Of the oxidizing biocides, chlorine is the most widely used to treat recirculating water systems. The chemistry of chlorine well known. When added to water, chlorine can exist in either of two forms, HOCl and OCl$^-$, depending on pH. These chemical species of chlorine, also referred to as "free chlorine," react with a wide variety of compounds in aqueous systems.

The highly reactive nature of chlorine may also be a liability, as some of the oxidizer will be used (e.g., consumed) during reactions with non-biological material. Therefore, in order to provide enough oxidizer to react with microorganisms in a process stream, the total amount of oxidizer needed to inhibit microorganisms will include that used in reactions with non-biological components of the system. Reactions with non-biological components of process water not only add to treatment cost, but undesired by-products can be generated and other additives in the process stream can be adversely affected.

Process streams such as in paper mills are especially problematic for highly reactive oxidizers because of the high concentrations of dissolved and particulate inorganic and organic materials. Such process waters exhibit a very high "demand" on the oxidizer. "Demand" is defined as the amount of chlorine that reacts with substances other than the target microorganisms in the process water. In order to maintain an effective concentration of chlorine in an aqueous system to inhibit microorganisms, an amount in excess of the demand must be applied. The types and amounts of inorganic and organic materials in a process stream will define the demand for an oxidizer. For example, many substances are known to react with chlorine and result in the chlorine being non-biocidal; such substances include sulfides, cyanides, metal ions, lignin, and, among others, various water treatment chemicals (e.g., some scale and corrosion inhibitors).

Although effective as biocides, strong oxidizers such as sodium hypochlorite can cause many problems in an industrial process stream such as increased corrosion rates, increased consumption of wet end additives, and, among others, decreased life of felts used on paper machines.

Because of the inherent reactivity of chlorine and related strong oxidizers with non-biological organic and inorganic materials, it is desirable to have the oxidizer in a form that would have antimicrobial activity but be less reactive with non-biological materials. Therefore, the process of chloramination has been used to avoid some of the problems associated with the use of strong oxidizers. Chloramination can occur by either (1) adding chlorine to a water system that contains a known, low concentration of ammonia, or (2) adding ammonia to a water system that contains a known, low concentration of chlorine. In either situation, the chlorine and ammonia will react in situ to form a chloramine. Chloramines generated from reacting chlorine and ammonia include monochloramine ($NH_2Cl$), dichloramine ($NHCl_2$), and trichloramine ($NCl_3$). Two of the important parameters that determine which chloramine species will exist in a system are pH and the ratio of Cl to N.

Chlorine, as a gas or liquid, and ammonia are commonly combined to form chloramines. However, other substances containing an amine ($RNH_2$) group can also form chloramines. The antimicrobial activity of a chloramine depends on the chemical nature of the amine-containing compound. For example, ammonium hydroxide can react with an oxidizing halogen donor such as sodium hypochlorite to form monochloramine; this chloramine will be an effective biocide. However, if an amino acid, such as glycine ($NH_2CH_2COOH$) is reacted with sodium hypochlorite, the amine group will be chlorinated, forming a mono- or di-chloramine species. The chlorinated glycine has less antimicrobial activity compared to monochloramine generated from ammonium hydroxide.

Chloramines are attractive for water treatment because of their stability in situ, ease of application and monitoring, and low capital and operational costs. Monochloramine is the preferred chemical species for disinfecting a water supply. Dichloramine is reported to be a superior disinfectant but has negative properties such has high volatility and odor.

The difference in reactivity and specificity of chlorine and monochloramine may allow the latter to penetrate a biofilm and react with the denizens whereas the former is consumed in non-specific reactions with materials in the water or abiotic components of the biofilm before it fully penetrates the biofilm.

Monochloramine is used as a single active to treat water for controlling growth of microorganisms in water and wastewater systems. Studies have shown that the pH of an aqueous system affects efficacy of monochloramine; the efficacy increases as pH decreases. Other physical and chemical parameters of a system can affect efficacy of chloramines by influencing the stability of the compounds. Parameters such as pH, temperature, and the presence of other chemicals have influence on the stability of monochloramine in water; at pH 7.5, the half-life of monochloramine is about 75 hours at 35 C but it is greater than 300 hours at 4 C.

Although widely practiced for treating municipal water distribution systems, chloramines are not commonly used in industrial systems. Chlorine (in bleach or chlorine gas) was used in combination with ammonia in papermaking systems. There was a shift toward using other oxidizing and non-oxidizing biocides in papermaking systems in subsequent years. However, recently there appears to be renewed interest in using chloramines in papermaking systems (see U.S. Pat. Nos. 6,478,973; 6,132,628; 5,976,386, the contents of each is herein incorporated by reference). For example, it has been shown that ammonium bromide reacted with sodium hypochlorite produces an effective biocide for industrial applications (U.S. Pat. No. 5,976,386, the content of which is herein incorporated by reference). Furthermore, this biocide is especially effective for controlling problems associated with microbial growth in pulp and paper process waters that have a pH in the alkaline range. The biocide generated from ammonium bromide, reported by Barak as "bromide-activated chloramine," effectively reduces the total microbial community within a system (i.e., biofilm-associated as well as planktonic bacteria) where the pH is neutral to alkaline. Barak teaches that the preferred pH of the receiving water should be in the range of 7 to 9; the biocide is effective in alkaline paper process water but does not interfere with other pulp and paper process and functional additives (e.g., wet and dry strength additives, size agents, dyes, etc), unlike other common oxidizer programs.

There remains a need for improved biocides that are effective under harsh environmental conditions such as found in the papermaking industry and other industrial processes.

SUMMARY OF THE INVENTION

The present invention comprises a method for producing a synergistic mixture (or combination) of monohaloamine and dihaloamine. The present invention is directed to methods and equipment to produce certain synergistic combinations of haloamines and introduce said combinations to industrial process streams for controlling growth of microorganisms in aqueous systems and for controlling the problems resulting from uncontrolled growth of microorganisms in industrial process systems. More specifically, the present invention relates to an apparatus and methods to produce certain mixtures (or combinations) useful to prevent growth of microorganisms in industrial process waters.

More specifically the method of this invention comprises producing method for producing an aqueous solution containing a synergistic combination of monohaloamine and dihaloamine biocide to control growth of microorganisms in an aqueous system which comprises a) contacting an ammonium or an amine source with a halogenated oxidant in amounts of each effective to produce monohaloamine, and
b) reducing the pH to convert a desired portion of the monohaloamine to dihaloamine.

The present invention relates to certain combinations, apparatus and processes useful for controlling the growth of microorganisms in aqueous systems and for controlling the problems resulting from uncontrolled growth of microorganisms in industrial process waters.

BRIEF DESCRIPTION OF THE FIGURES

FIG. 1 Apparatus for producing synergistic mixture of biocide.
FIG. 2 Absorbance of Chloramine at various pH values.
FIG. 3 Apparatus for producing synergistic mixture of biocide.
FIG. 4 pH adjustment of Chloramine at various time intervals.
FIG. 5 pH adjustment of Chloramine at various time intervals.

DETAILED DESCRIPTION OF THE INVENTION

For the purposes of this invention, haloamines are defined as chemicals with a composition that includes one or more halogen atoms associated with an amine group and possess antimicrobial activity. The nitrogen may or may not be bonded to another atom other than hydrogen. Halogens include chlorine, bromine, iodine, and fluorine. All can be used in the apparatus and methods described herein to treat industrial process waters, but chloramines are preferred.

The apparatus and methods described herein are useful for producing microbiocidal mixtures (or combinations) of haloamines that possess a high degree of antimicrobial activity which could not have been predicted from the known activities of the individual ingredients comprising the combinations. The enhanced activity of the mixtures (or combinations) permits a significant reduction in the total quantity of the biocide required for an effective treatment of an aqueous system.

The present invention includes an apparatus for producing synergistic mixtures (or combination) containing monohaloamine and dihaloamine. Haloamines are produced by combining an amine source or ammonium source with a halogenated oxidant or in the alternative combining an amine source or ammonium source with an oxidant in the presence of a halogen source. The halogen source can be a salt or can be from the ammonium source such as ammonium chloride. Examples of haloamines are chloramines (monochloramine or dichloramine) and bromamines (monobromamine and dibromamine).

The amine sources or ammonium sources used in the present invention include, but are not limited to, ammonia and ammonium salts and amines. What is meant by ammonium salts are those salts that have a $NH_4^+$ cation and a related anion. Examples of ammonium salts include, but are not limited to, ammonium acetate, ammonium bicarbonate, ammonium bifluoride, ammonium bromide, ammonium carbonate, ammonium chloride, ammonium citrate, ammonium fluoride, ammonium hydroxide, ammonium iodide, ammonium molybdate, ammonium nitrate, ammonium oxalate, ammonium persulfate, ammonium phosphate, ammonium sulfate, ammonium sulfide, ferric ammonium sulfate, ferrous ammonium sulfate and ammonium sulfamate. Preferred ammonium salts are ammonium carbonate, ammonium citrate, ammonium hydroxide, ammonium sulfate and ammonium chloride. Quaternary ammonium salts are not considered amine sources for the present invention and are not included in the term ammonium salts for the purposes of this invention.

The amine sources useful in the present invention can also be primary amines ($RNH_2$), secondary amines ($R_2NH$) or tertiary amines ($R_3N$). Additional ammonium and/or amine sources included ammonia, dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallow-methylamine, coco-methylamine, n-alkylamines, n-acetylglucosamine, diphenylamine, ethanolmethylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, polyamines, primary amines, secondary amines, cyclic amines, bicyclic amines, oligocyclic amines, aliphatic amines, aromatic amines, primary and secondary nitrogen containing polymers. Quaternary amine are not included in the amine source useful in this invention. Quaternary amines are saturated and unreactive with the oxidants. They do not react sufficiently to produce the biocide of the present invention.

Oxidants are reacted with the amine sources to produce the biocides. The oxidants used include, but are not limited to, chlorine, hypochlorite, hypochlorous acid, chlorine dioxide, chlorinated isocyanurates, bromine, hypobromite, hypobromous acid, bromine chloride, electrolytically-generated chlorites, electrolytically-generated bromites, halogenated hydantoins, ozone, and peroxy compounds such as perborate, percarbonate persulfate, hydrogen peroxide, percarboxylic acid, and peracetic acid.

In one particular variant of the invention, the amine source or ammonium source is ammonium hydroxide and the oxidant is sodium hypochlorite.

In another particular variant of the invention, the amine source or ammonium source is ammonium sulfate and the oxidant is sodium hypochlorite.

The biocidal mixtures prepared by the methods of this invention are effective for controlling and inhibiting the growth and reproduction of microorganisms in aqueous systems and additive aqueous systems. Aqueous systems include industrial waters systems such as cooling water systems, pulp and paper systems, petroleum operations, industrial lubricants and coolants, lagoons, lakes, and ponds. In addition, the aqueous systems in which the present invention can be used includes, but is not limited to, those involved in, paints, leather, wood, wood pulp, wood chips, starch, clays, retention aids, sizing agents, defoamers, dry and wet strength additives, pigment slurries (e.g., precipitated calcium carbonate), proteinaceous materials, lumber, animal hides, vegetable tanning liquors, cosmetics, toiletry formulations, emulsions, adhesives, coatings, metalworking fluids, swimming pool water, textiles, heat exchangers, pharmaceutical formulations, geological drilling lubricants, and agrochemical compositions.

Aqueous systems include additive aqueous systems. "Additive" is defined as a product or substance dissolved or suspended in water that is or will be added into a larger aqueous system. Examples of additives used in the pulp and paper industry include, but are not limited to, retention aids, sizing agents, defoamers, dry and wet strength additives and pigment slurries.

The dosage amounts of the monohaloamine and dihaloamine required for effectiveness of the products made by the method of this invention generally depend on the nature of the aqueous system being treated, the level of organisms present in the aqueous system, and the level of inhibition desired. A person skilled in the art, using the information disclosed herein could determine the amount necessary without undue experimentation.

Effective concentrations of monohaloamine, such as chloramine, on an active level basis, are from about 0.01 milligram per liter (mg/l) to about 1000 mg/l by weight, (i.e., based on the weight of monohaloamine as measured by the amount of available chlorine [in mg/l]) and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. The amount of dihaloamine, on an active level basis, is from about 0.01 parts per million (mg/l) to about 1000 mg/l by weight (i.e., based on the weight of dihaloamine as measured by the amount of available chlorine [in mg/l]), and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. Thus, with respect to the biocides, the lower and upper limits of the required concentrations substantially depend upon the system to be treated.

FIG. 1 is a block diagram illustrating one form of the apparatus constructed in accordance with the present invention. As used herein below, a "batch quantity" refers to a volume of a solution or suspension that is produced in a series of discrete stages (or steps) in a reservoir or container.

The apparatus illustrated in FIG. 1 is intended to produce a batch quantity of a haloamine, part of which is subsequently converted to a second haloamine species that is then recombined with the first haloamine and injected into an aqueous system to be treated for controlling growth of microorganisms. In one particular advantageous embodiment of the invention, a batch quantity of monochloramine is produced in a reservoir. The pH of the monochloramine solution is then decreased to a desired value during which, a known amount of the monochloramine is converted to dichloramine. The synergistic mixture is used to treat a liquid, such as water in an industrial process system, in such a manner as to inhibit growth of microorganisms in said water.

The synergistic combination of haloamines is produced by the following steps: (1) opening valve 1 to add a desired volume of water through water line 2 into reservoir 3 and providing agitation or mixing with mixer 4; (2) adding a desired quantity of a concentrated amine source from reservoir 5 via line 6 with pump 7 in to achieve a desired concentration in reservoir 3; and (3) adding an halogen source from reservoir 8 via line 9 with pump 10 in sufficient quantity to achieve a desired concentration in reservoir 3. The pH of the monohaloamine solution in reservoir 3 is measured with pH probe 11 connected to a pH controller 12 that controls pump 13. The pH of the monohaloamine solution in reservoir 3 is decreased to a predetermined value by addition of the appropriate quantity of an acid solution from reservoir 14 via conduit 15. After the batch quantity of the mixed haloamine solution is prepared in the aforementioned manner, pump 16 transfers the solution through conduit 17 to one or more addition points in the process water 18. An optional in-line monitoring method entails diverting a portion of the solution through conduit 19 whereby the solution passes through spectrophotometer 20 wherein the absorbance spectral profile of the solution is determined. Conduit 19 also functions to return the solution to conduit 17 before it enters the water to be treated at location 18.

FIG. 2 illustrates how the composition of a batch solution of the monohaloamine, changes as a function of pH. In this case, a 100 ppm monochloramine solution was prepared at pH 8.0 and had a single peak with an absorbance maximum at 244 nm. As the pH was decreased by addition of a hydrochloric acid solution, the 244 nm peak decreased in height, indicating a decrease in monochloramine concentration and there was an increase in absorbance value at 295 nm. Dichloramine has two absorbance maxima –206 nm and 295 nm. The peak at 295 nm represents the formation of dichloramine.

FIG. 3 is a block diagram illustrating another form of apparatus constructed in accordance with the present invention.

The apparatus illustrated in FIG. 3 is intended to produce a batch quantity of a haloamine, part of which is subsequently converted to a second haloamine species that is then recombined with the first haloamine and injected into a liquid to be treated for controlling growth of microorganisms. In one particular advantageous embodiment of the invention, a batch quantity of monochloramine is produced in a reservoir. The monochloramine solution is then used as one part of a synergistic mixture. The other part of the synergistic mixture, dichloramine, is produced in-line as the monochloramine is pumped from the reservoir wherein it was produced. The synergistic mixture is used to treat a liquid, such as water in an industrial process system, in such a manner as to inhibit growth of microorganisms in said water. A batch quantity refers to a volume of a biocide mixture that is produced in a series of discrete stages (or steps) in a reservoir or container. The synergistic combination of haloamines is added to the water to be treated.

In FIG. 3 The synergistic combination of haloamines is produced by the following steps: (1) opening valve 1 to add a desired volume of water through water line 2 to reservoir 3 and providing constant agitation with mixer 4; (2) adding a desired quantity of a concentrated amine source from reservoir 5 via line 6 with pump 7 in to achieve a desired concentration in reservoir 3; and (3) adding an halogen source from reservoir 8 via line 9 with pump 10 in sufficient quantity to achieve a desired concentration in reservoir 3. After the haloamine solution is prepared in reservoir 3, the solution is pumped from reservoir 3 through line 11 with pump 12. A fraction of the solution in line 11 is diverted to line 15 by valve 13 using pump 14 into mixing chamber 6. The solution in mixing chamber 16 is constantly agitated with mixer 17. The pH of the solution in mixing chamber 16 is monitored with pH probe 18 connected to pH meter/controller 19 and maintained at a desired value (e.g., 3.5) by a pumping dilute acid solution from reservoir 20 with pump 21. The solution in mixing chamber 16 is pumped at a specific rate through line 22 with pump 23, through valve 24, into line 11. An optional in-line monitoring methods includes diverting a portion of the solution through line 25 whereby the solution passes through spectrophotometer 26 wherein the absorbance spectral profile of the solution is determined. Line 25 also functions to return the solution to line 11 before it enters the water to be treated at location 27.

The amine source in reservoir 5 can be any of the aforementioned amine salts or amine-containing compounds. Non-halogen-containing, inorganic amine sources such as ammonium sulfate and ammonium hydroxide are preferred.

In one particular advantageous embodiment of the invention, the haloamine solution in reservoir 3 is prepared in batch form as a concentrated solution that has a total haloamine concentration in the range of 100 mg/l to 10,000 mg/l, preferably from 500 mg/l to 8000 mg/l. More preferably, the haloamine solution is prepared in batch form as a concentrated solution that has a haloamine concentration in the range of 1,000 mg/l to 5,000 mg/l.

During production of the synergistic haloamine solution, in FIG. 3, a fraction of the haloamine solution is diverted through valve 13 whereby that fraction of the haloamine solution is added to mixing chamber 16 wherein the pH is adjusted in the range of between about 3.0 to about 5.0. In one particular advantageous embodiment of the invention, the pH is adjusted in the range of between 3.5 and 4.0.

In one particular advantageous embodiment of the invention, in FIG. 3, the haloamine solution in reservoir 3 is monochloramine. By passing part of the monochloramine solution through mixing chamber 16, monochloramine is quantitatively converted to dichloramine as a result of pH being maintained in the range of about 3.0 to about 5.0 by addition of appropriate quantities of acid from reservoir 20. After the dichloramine solution is returned to line 11 through valve 24, the synergistic mixture of monochloramine and dichloramine is added to the receiving water at location 27. The ratio of monochloramine to dichloramine is controlled by the flow rate of solution through mixing chamber 16.

In one particular advantageous embodiment of the invention, a controller can be used to automate production of batches of synergistic combinations of haloamines.

In one particular advantageous embodiment of the invention, the mixing chamber can be used to change parameters other than pH to cause formation of another chemical species of haloamine that is a component of the synergistic mixture. For example, it is possible to modify the chlorine to nitrogen ratio to cause conversion of monochloramine to dichloramine.

The ratio of haloamines in the biocidal mixture required for effectiveness in this invention generally depends on the nature of the aqueous system being treated, the level of organisms present in the aqueous system, and the level of inhibition desired. A person skilled in the art, using the information disclosed herein could determine the amount necessary without undue experimentation.

In one particular advantageous embodiment of the invention, the effective ratios of haloamines in the biocide are from about 1:100 (monohaloamine to dihaloamine) to 100:1 (monohaloamine to dihaloamine). In another advantageous embodiment of the invention, the effective ratios of haloamines are from about 1:20 (monohaloamine to dihaloamine) to 20:1 (monohaloamine to dihaloamine).

A preferred embodiment of the invention includes monochloramine and dichloramine as the haloamine chemical species. With respect to the ratios of monochloramine to dichloramine to yield a synergistic biocide product, the lower and upper limits of the required ratios substantially depend upon the system to be treated.

In one advantageous embodiment, in either of FIG. 1 or 3 the amine source and the halogenated oxidizer source are simultaneously added to the dilution water in reservoir 3.

In another embodiment, the apparatus can be used to produce batch quantities of a haloamine and then generate the synergistic mixture in such a way as to feed the synergistic mixture continuously or intermittently to aqueous systems.

The apparatus described herein can be used to produce and administer a synergistic combination of haloamine that can be added to the system as independent material(s) or in combination with other materials being added to the aqueous system being treated system. For example, the apparatus and methods can be used to produce and deliver a synergistic combination of monochloramine and dichloramine in water or via other solutions such as starch, clay, pigment slurries, precipitated calcium carbonate, retention aids, sizing aids, dry and/or wet strength additives, defoamers or other additives used in the manufacturing of pulp or paper products.

A preferred embodiment of the invention includes use of a controller for production of batches of the synergistic combination of haloamines according to a pre-determined schedule.

In another preferred embodiment of the invention, production of batches of the synergistic combination of haloamines is coordinated to water flow or product production in an industrial setting in a manner to provide effective doses of the haloamines on an as needed basis.

The apparatus and methods described herein is useful for biocide addition to industrial process waters in manners that are dependent on growth of the microbial population, the type of problematic microorganisms and the degree of surface fouling in a particular system. The haloamine solution can be added on an intermittent basis according to a pre-determined schedule or an "on demand" basis according to flow rate of an industrial process water or amount of product being produced.

The apparatus and methods described herein will be used for biocide addition to industrial process waters wherein the biocide is added directly to the process water stream or to additive systems. Such additive systems include but are not limited to starch makedown solutions, retention aid makedown solutions, precipitated calcium carbonate slurries. The biocide of the present invention can be added at various feed points within the aqueous system to be treated. Examples of feed point in a pulp and paper system include, but are not limited to short or long loop, broke chest, saveall, thick stock, blend chest and head box.

EXAMPLES

The following examples are intended to be illustrative of the present invention. However, these examples are not intended to limit the scope of the invention or its protection in any way. The examples illustrate how the apparatus and methods described herein can be used to produce a combination of haloamines in a synergistic biocide for use to control bacteria in industrial process water.

Example 1

The efficacies of the individual haloamines and the synergistic combination produced with the apparatus described above were determined using a consortium of microorganisms and a dose-response protocol. Concentrations of monochloramine and dichloramine reported herein are in units of milligrams per liter as measured by $Cl_2$ analysis; the Hach DPD chlorine test (Hach Company, Loveland, Colo.) was used to measure the total available chlorine concentrations and are expressed as milligrams per liter as $Cl_2$. The DPD assay is based on the amount of chlorine in a sample that reacts with N,N-diethyl-p-phenylenediamine oxalate. To determine the amount of monochloramine or dichloramine in a sample, an aliquot of the sample was transferred to a clean container, diluted with deionized water, as appropriate, and assayed according to the Hach DPD chlorine test. The assay measures the total amount of chlorine that can react with the indicator reagent. The reaction is measured by determining the absorbance of light at 530 nm. Therefore, for the purposes of this invention, a quantity of monochloramine or dichloramine presented in units of mg/l signifies that amount of monochloramine or dichloramine that contains the designated amount of milligrams per liter of reactive chlorine. Thus, for example, a sample treated with 1 mg/l monochloramine or dichloramine will contain a total available chlorine concentration of 1 mg/l. Similarly, a sample treated with 0.5 mg/l monochloramine and 0.5-mg/l dichloramine will contain a total available chlorine concentration of 1 mg/l.

Use of the term "ratio" in regard to the active molecules tested is based on the amount of each of two biocidally-active chemicals on a milligram per liter basis. For example, a solution containing a 1:1 ratio of monochloramine to dichloramine would contain X mg/l (as $Cl_2$) of monochloramine and X mg/l (as $Cl_2$) dichloramine, where X=a fraction or whole number. Likewise, a solution containing a 4:1 ratio of monochloramine to dichloramine would contain 4X mg/l (as $Cl_2$) of monochloramine and X mg/l as $Cl_2$) dichloramine, where X=a fraction or whole number.

The materials were tested against multi-species bacterial consortium (also referred to as an artificial consortium) containing approximately equal numbers of six bacterial strains. Although the test strains are representative of organisms present in paper mill systems; the effect is not limited to these bacteria. Two of the strains were *Klebsiella pneumonia* (ATCC 13883) and *Pseudomonas aeruginosa* (ATCC 15442). The other four strains were isolated from papermill systems and have been presumptively identified as *Curtobacterium flaccumfaciens, Burkholderia cepacia, Bacillus maroccanus,* and *Pseudomonas glathei*. Each strain was grown on Tryptic Soy Agar overnight at 37° C. Sterile cotton-tipped swabs were used to aseptically transfer cells to a sterile solution of saline. Each cell suspension was prepared to a desired concentration as measured by turbidity before equal volumes of each of the cell suspensions were then combined to prepare the consortium.

In this example, the apparatus and methods described herein were used to produce a synergistic haloamine biocide solution that contained monochloramine and dichloramine in the ratio of 4 to 1. The first step in producing the synergistic mixture was to combine an amine and halogen in the proper ratio to result in formation of a desired concentration of a haloamine. Reservoir 3 of FIG. 3 was charged with an appropriate volume of deionized water immediately before solutions of the amine source in reservoir 5 and the halogen source in reservoir 8 were sequentially pumped into the deionized water in reservoir 3. The volumes of the amine and halogen sources added to the deionized dilution water in reservoir 3 were such that the amine functionality ($-NH_2$) and the chlorine ($Cl^-$) were in equimolar concentrations. In the example, the batch solution of monochloramine ($NH_2Cl$) in reservoir 3 was 1000 mg/l. To form this concentration of monochloramine, the amine source was ammonium sulfate ($[NH_4]_2SO_4$) and the halogen source was sodium hypochlorite (NaOCl). Stock solutions of ammonium sulfate and sodium hypochlorite were prepared and added to reservoirs 5 and 8, respectively. The volumes of each stock solution added to the deionized dilution water in reservoir 3 were calculated based on the concentration of each when the monochloramine solution was prepared. For each stock solution, the volume added to reservoir 3 was such that in the final volume, the concentration of the amine group and the active chlorine was 19.6 millimolar. The concentration of monochloramine in reservoir 3 was confirmed by measuring total chlorine concentration by the Hach DPD chlorine test. Also, the presence of the active chemical species produced with the apparatus and methods described herein was demonstrated with a scanning spectrophotometer by measuring absorbance of light in the range of 200 nm to 350 nm.

The next step in producing the synergistic mixture of haloamines was to begin pumping the monochloramine solution in reservoir 3 through line 11. As the solution was pumped through line 11, a portion of the solution flow was diverted through a spectrophotometer 26 equipped with a quartz flow-cell and the absorbance spectrum was measured. As the haloamine solution was pumped directly from reservoir 3 without a portion passing through mixing chamber 16, the absorbance profile did not change (FIG. 4). To produce the synergistic mixture, a portion of the haloamine solution was diverted by valve 13 into mixing chamber 16 where, in the case of chloramines, the low pH resulted in monochloramine being converted to dichloramine. The dichloramine solution was returned to line 11 via valve 24. As the concentration of dichloramine in the feed stream increased to a constant value, there was a gradual decrease in the absorbance peak at 244 nm (characteristic of monochloramine) with concomitant increases in absorbance readings in the 206 nm and 295 nm regions (characteristic of dichloramine). The changes in spectral profiles of the monochloramine solution as dichloramine was produced to generate the synergistic combination are consistent with published spectra of monochloramine and dichloramine. As illustrated in FIG. 4, in a solution of monochloramine and dichloramine in a ratio of 4 parts monochloramine to 1 part dichloramine, there was a time-dependent decrease in absorbance at 244 nm and concomitant increases in absorbance values at 206 and 295 nm. In this example, the monochloramine concentration in reservoir 3 was 1000 mg/l. The monochloramine solution was pumped from reservoir 3 at a flow rate of 10 ml per minute. Twenty percent of the pumped volume (i.e., 2 ml/min) was diverted to the mixing chamber 16 where the pH was maintained at a value of 4.0 to convert the monochloramine to dichloramine and returned to the monochloramine stream at the same rate (2 ml/min). In the case of the 4:1 ratio of monochloramine to dichloramine, the absorbance readings at 244 nm reached a stable reading after about 16 minutes, indicating an equilibrium point had been attained.

A sample of the biocide solution was aseptically collected at the end of line 11 after the apparatus had been operated for approximately 20 minutes and used in an efficacy assay. Samples of the monochloramine solution in reservoir 3 and the dichloramine solution in mixing chamber 16 were also collected to test efficacy of each active. In the assay, the bacterial consortium was prepared as described above and an appropriate quantity of the cell suspension was aseptically transferred to sterile saline with pH adjusted to selected values. The cells were then challenged with the haloamines and synergistic combinations of the haloamines. In each case, the total halogen concentration was 0.5 mg/l (as $Cl^-$).

In this example, in addition to untreated control, the consortium was exposed to the following treatments: (1) 0.5 mg/l of monochloramine; 0.5 mg/l dichloramine; (3) 0.25 mg/l monochloramine plus 0.25 mg/l dichloramine; and (4) 0.4 mg/l monochloramine plus 0.1 mg/l dichloramine. The consortium was exposed to the haloamines for 20 minutes before samples were removed for cell enumeration by the spread plate technique. Exposing the consortium to the selected pH values did not cause changes in the cell counts. The control counts presented in Table 1 are those obtained after a 20 minute exposure to saline with pH adjusted to the indicated value. Exposing the consortium to 0.5 mg/l monochloramine or 0.5 mg/l dichloramine resulted in decreased cell counts; the decrease was significantly larger at lower pH values. Exposing the consortium to a 4:1 ratio of monochloramine to dichloramine caused the greatest decline in bacterial counts.

Table 1 shows the population sizes of a bacterial consortium following a 20 minute exposure to monochloramine (MCA) and/or dichloramine (DCA). Numbers represent $\log_{10}$ colony counts and represent the average of three values.

TABLE 1

| pH | Untreated Control | 0.5 mg/l MCA | 0.5 mg/l DCA | 0.25 mg/l MCA + 0.25 mg/l DCA | 0.4 mg/l MCA + 0.1 mg/l DCA |
|---|---|---|---|---|---|
| 8 | 5.30 | 5.36 | 5.19 | 5.09 | 5.04 |
| 7 | 5.34 | 5.06 | 5.01 | 4.02 | 4.09 |
| 6 | 5.39 | 4.94 | 5.16 | 4.02 | 3.73 |
| 5 | 5.40 | 4.93 | 3.50 | 2.87 | 2.22 |

These results demonstrated the apparatus and methods described herein were effective at producing a synergistic haloamine biocide that consisted of monochloramine and dichloramine in a 4:1 ratio.

Example 2

The apparatus was used to produce the synergistic biocide in which the ratio of monochloramine to dichloramine was changed by adjusting the flow rate of monochloramine through mixing chamber 16. In this example, the flow rate was incrementally adjusted in a manner to allow the ratio of monochloramine to dichloramine to be 9 parts monochloramine to 1 part dichloramine. Each incremental change was carried out in a manner to allow for the absorbance spectrum (FIG. 5) to become stable at which time samples of the 9 to 1 (monochloramine to dichloramine) biocide mixture as well as the monochloramine solution in reservoir 3 and the dichloramine solution in mixing chamber 16 were collected. The total chlorine concentration of each sample was determined to confirm the ratio was correct. Samples of the monochloramine and dichloramine solutions were mixed in appropriate volumes to obtain the 1:1 and 4:1 ratios.

The dose-challenge studies were carried out as previously described using a freshly prepared bacterial consortium. Sterile saline was prepared with pH adjusted to values of 5.0, 6.0, 7.0 and 8.0. The initial concentration of bacteria in the consortium was approximately $2\times10^5$ per milliliter. The cell suspensions were challenged with 0.5 mg/l (as $Cl_2$) active with each synergistic chloramine solution. Numbers of surviving bacteria were determined after a 20-minute contact time. As illustrated in Table 2, as the ratio of monochloramine to dichloramine changed, the relative efficacy also changed. Numbers are reported as $Log_{10}$ transformations of the plate counts. The most effective ratio of monochloramine to dichloramine was in the range of 9:1 (monochloramine to dichloramine) to 2:1 (monochloramine to dichloramine).

Table 2 shows the results of efficacy testing of selected ratios of monochloramine to dichloramine. Cells were exposed to the indicated concentration of monochloramine (MCA) and/or dichloramine (DCA) for 20 minutes before counting the numbers of surviving cells

TABLE 2

| pH | Control | 0.5 mg/l MCA | 0.5 mg/l DCA | 0.25 mg/l MCA + 0.25 ppm DCA | 0.4 mg/l MCA + 0.1 ppm DCA | 0.45 mg/l MCA + 0.05 ppm DCA |
|---|---|---|---|---|---|---|
| 8 | 5.42 | 5.41 | 5.24 | 5.09 | 5.11 | 5.38 |
| 7 | 5.45 | 5.13 | 5.07 | 4.01 | 4.09 | 4.53 |
| 6 | 5.49 | 4.84 | 5.16* | 4.01 | 3.72 | 4.41 |
| 5 | 5.54 | 5.03 | 3.56 | *N.D. | N.D. | N.D. |

N.D. = none detected

This example demonstrates that the apparatus and methods described herein can be used to change the ratio of actives in the synergistic mixture in such a manner that said mixture can be optimized for use as a biocide depending on the characteristics of the liquid to be treated.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention

What is claimed is:

1. A method for producing an aqueous solution containing a synergistic combination of monohaloamine and dihaloamine biocide to control growth of microorganisms in an aqueous system which comprises
    a) contacting an ammonium or an amine source with a halogenated oxidant in water in amounts of each effective to produce monohaloamine, and
    b) converting a portion of the monohaloamine to a desired amount of dihaloamine by reducing the pH to a desired value below 7.0 thereby converting a desired portion of the monohaloamine to dihaloamine.

2. The method of claim 1, wherein the ammonium or amine source is ammonia, ammonium hydroxide or an ammonium salt.

3. The method of claim 2 wherein the ammonium salt is selected from the group consisting of aluminum ammonium sulfate, ammonium acetate, ammonium bicarbonate, ammonium bifluoride, ammonium bromide, ammonium carbonate, ammonium chloride, ammonium citrate, ammonium fluoride, ammonium iodide, ammonium molybdate, ammonium nitrate, ammonium oxalate, ammonium persulfate, ammonium phosphate, ammonium sulfate, ammonium sulfide, ferric ammonium sulfate, ferrous ammonium sulfate, and combinations thereof.

4. The method of claim 2 wherein the amine source is selected from the group consisting of polyamines, primary amines, secondary amines, cyclic amines, bicyclic amines, oligocyclic amines, aliphatic amines, aromatic amines, primary and secondary nitrogen containing polymers and combinations thereof.

5. The method of claim 4 wherein the amine source is selected from the group consisting of dimethylamine, ethanolamine, ethylenedlamine, diethanolamine, triethanolamine, dodecylethanalamine, hexdecylethanolamine, oleic acid ethanolamine, triethylenetetramine, dibutylamine, tributylamine, glutamine, dilaurylamine, distearylamine, tallow-methylamine, coco-methylamine, n-acetylglucosamine, diphenylamine, ethanolmethylamine, diisopropanolamine, n-methylamine, n-hexyl-n-methylamine, n-heptyl-n-methylamine; n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, and combinations thereof.

6. The method of claim 2 wherein the halogenated oxidant is selected from the claim consisting of chlorine, hypochlorite, hypochlorous acid, chlorinated isocyanurates, bromine, hypobromite, hypobromous acid, bromine chloride, halogenated hydantoins, and combinations thereof.

7. The method of claim 1 wherein the ammonium or amine source is ammonium sulfate and the halogenated oxidant is a hypochlorite salt.

8. The method of claim 1 wherein, the halogenated oxidant is a chlorinated oxidant and the pH in step b) is adjusted until the ratio of monochloramine to dichloramine is 200:1 to 1:100.

* * * * *